United States Patent [19]

Larson et al.

[11] Patent Number: 5,609,575

[45] Date of Patent: Mar. 11, 1997

[54] INFUSION PUMP AND METHOD WITH DOSE-RATE CALCULATION

[75] Inventors: Stella D. Larson, Columbus Township, Anoka County; Anne F. Mickelson, Woodbury; Peter M. Eisenberg, Minneapolis, all of Minn.

[73] Assignee: Graseby Medical Limited, Watford, United Kingdom

[21] Appl. No.: 417,434

[22] Filed: Apr. 4, 1995

Related U.S. Application Data

[63] Continuation of Ser. No. 225,753, Apr. 11, 1994, abandoned.

[51] Int. Cl.$^6$ ............................................. A61M 1/00
[52] U.S. Cl. ......................................................... 604/65
[58] Field of Search .......................... 604/30–34, 49–53, 604/65–67, 118, 151, 250–253; 128/DIG. 13, DIG. 14

[56] References Cited

U.S. PATENT DOCUMENTS

| | | | |
|---|---|---|---|
| 3,685,697 | 8/1972 | Caslow et al. | 222/137 |
| 3,771,694 | 11/1973 | Kaminski | 222/70 |
| 3,809,871 | 5/1974 | Howard et al. | 235/151.3 |
| 3,901,231 | 8/1975 | Olson | 128/214 F |
| 3,908,652 | 9/1975 | Weissinger | 128/214 E |
| 3,966,358 | 6/1976 | Heimes et al. | 417/12 |
| 3,985,133 | 10/1976 | Jenkins et al. | 128/214 F |
| 3,990,444 | 11/1976 | Vial | 128/214 F |
| 4,085,747 | 4/1978 | Lee | 128/214 F |
| 4,187,057 | 2/1980 | Xanthopoulos | 417/63 |
| 4,210,138 | 7/1980 | Jess et al. | 128/214 E |
| 4,256,437 | 3/1981 | Brown | 417/45 |

(List continued on next page.)

FOREIGN PATENT DOCUMENTS

| | | |
|---|---|---|
| 0179587 | 4/1986 | European Pat. Off. . |
| 715977 | 4/1980 | France . |
| 2921066A1 | 11/1980 | Germany . |
| 3015777A1 | 10/1981 | Germany . |
| 3442774A1 | 5/1986 | Germany . |
| 2109474 | 6/1983 | United Kingdom . |
| 93/24893 | 12/1993 | WIPO . |

OTHER PUBLICATIONS

Horizon™ Modular Infusion System, Operation Manual, McGaw, Inc. (1992), pp. i–ii and 1–1 through 9–4.

Medfusion Model 2010, Medfusion Syringe Infusion Pump, Operations Manual, Medfusion Inc., Revision 1 (Jun. 1991), p. 1–68.

Pp. 36–41 of an infusion pump operation manual that was received by one of the inventors more than one year prior to the filing of the patent application.

12–page brochure entitled "The Horizon Modular Infusion System", McGaw, Inc.

1 sheet of operating instructions describing Horizon Dose Mode.

IMED 8–page brochure entitled "Gemini PC–4 Volumetric Pump/Controller".

Operator's Manual dated Feb. 15, 1993 for Gemini PC–4 Volumetric Pump/Controller, Table of Contents and pp. 1–57.

*Primary Examiner*—Manuel Mendez
*Attorney, Agent, or Firm*—Kinney & Lange, P.A.

[57] ABSTRACT

An infusion pump and method of operating an infusion pump in which the user of the infusion pump is prompted to input a number of infusion parameters, which include a dose mode, a drug dose, a drug amount, and a drug volume. After the parameters are input by the user, the infusion pump automatically calculates an infusion rate corresponding to the desired drug dose input by the user. The infusion pump, which includes a fluid pump, may round the calculated infusion rate to conform it to a flow rate which the fluid pump can deliver. If the infusion rate is rounded, the infusion pump calculates the actual drug dose from the rounded infusion rate and displays the actual dose on a visual display to allow the user of the infusion pump to determine how much the actual dose varies from the intended dose input by the user. After the actual dose is determined, the infusion pump continuously infuses the patient with the drug at the displayed infusion rate.

44 Claims, 7 Drawing Sheets

U.S. PATENT DOCUMENTS

| | | | |
|---|---|---|---|
| 4,270,532 | 6/1981 | Franetzki et al. | 128/213 R |
| 4,276,004 | 6/1981 | Hahn | 417/479 |
| 4,278,085 | 7/1981 | Shim | 128/214 F |
| 4,322,201 | 3/1982 | Archibald | 417/279 |
| 4,443,218 | 4/1984 | DeCant, Jr. | 604/67 |
| 4,457,751 | 7/1984 | Rodler | 604/66 |
| 4,519,792 | 5/1985 | Dawe | 604/152 |
| 4,529,401 | 7/1985 | Leslie et al. | 604/131 |
| 4,537,561 | 8/1985 | Xanthopoulos | 417/63 |
| 4,544,336 | 10/1985 | Faeser et al. | 417/412 |
| 4,617,014 | 10/1986 | Cannon et al. | 604/67 |
| 4,653,987 | 3/1987 | Tsuji et al. | 417/360 |
| 4,657,490 | 4/1987 | Abbott | 417/478 |
| 4,666,430 | 5/1987 | Brown et al. | 604/141 |
| 4,668,220 | 5/1987 | Hawrylenko | 604/155 |
| 4,671,792 | 6/1987 | Borsanyi | 604/153 |
| 4,685,903 | 8/1987 | Cable et al. | 604/154 |
| 4,689,043 | 8/1987 | Bisha | 604/250 |
| 4,690,673 | 9/1987 | Bloomquist | 604/67 |
| 4,692,145 | 9/1987 | Weyant | 604/65 |
| 4,714,462 | 12/1987 | DeDomenico | 604/67 |
| 4,725,205 | 2/1988 | Cannon et al. | 417/363 |
| 4,728,265 | 3/1988 | Cannon | 417/363 |
| 4,731,051 | 3/1988 | Fischell | 604/67 |
| 4,741,732 | 5/1988 | Crankshaw et al. | 604/50 |
| 4,741,736 | 5/1988 | Brown | 604/134 |
| 4,744,786 | 5/1988 | Hooven | 604/143 |
| 4,749,109 | 6/1988 | Kamen | 222/333 |
| 4,752,289 | 6/1988 | Balding et al. | 604/118 |
| 4,756,706 | 7/1988 | Kerns et al. | 604/66 |
| 4,758,228 | 7/1988 | Williams | 604/153 |
| 4,781,548 | 11/1988 | Alderson et al. | 604/153 |
| 4,785,799 | 11/1988 | Schoon et al. | 128/53 |
| 4,798,580 | 1/1989 | DeMeo et al. | 604/30 |
| 4,807,170 | 2/1989 | Kulli et al. | 364/413.01 |
| 4,808,167 | 2/1989 | Mann et al. | 604/151 |
| 4,838,860 | 6/1989 | Groshong et al. | 604/152 |
| 4,840,542 | 6/1989 | Abbott | 417/9 |
| 4,840,620 | 6/1989 | Kobayashi et al. | 604/246 |
| 4,846,637 | 7/1989 | Alderson et al. | 417/479 |
| 4,850,971 | 7/1989 | Colvin | 604/134 |
| 4,850,980 | 7/1989 | Lentz et al. | 604/248 |
| 4,856,339 | 8/1989 | Williams | 73/714 |
| 4,886,431 | 12/1989 | Soderquist et al. | 417/477 |
| 4,889,528 | 12/1989 | Nadai et al. | 604/65 |
| 4,890,984 | 1/1990 | Alderson | 417/234 |
| 4,898,578 | 2/1990 | Rubalcaba, Jr. | 604/66 |
| 4,898,579 | 2/1990 | Groshong et al. | 604/67 |
| 4,919,650 | 4/1990 | Feingold et al. | 604/67 |
| 4,925,444 | 5/1990 | Orkin et al. | 604/65 |
| 4,936,760 | 6/1990 | Williams | 417/479 |
| 4,943,279 | 7/1990 | Samiotes et al. | 604/51 |
| 4,966,579 | 10/1990 | Polaschegg | |
| 4,976,687 | 12/1990 | Martin | |
| 4,976,696 | 12/1990 | Sonderson et al. | |
| 4,978,335 | 12/1990 | Arthur, III | |
| 5,006,050 | 4/1991 | Cooke et al. | 417/ |
| 5,006,997 | 4/1991 | Reich | 364/ |
| 5,013,303 | 5/1991 | Tamari et al. | 604/ |
| 5,018,945 | 5/1991 | D'Silva | 417/ |
| 5,034,004 | 7/1991 | Crankshaw | 604/1 |
| 5,061,242 | 10/1991 | Sampson | 604/11 |
| 5,083,908 | 1/1992 | Gagnebin et al. | 417/47 |
| 5,104,374 | 4/1992 | Bishko et al. | 603/31 |
| 5,116,203 | 5/1992 | Natwick et al. | 417/53 |
| 5,131,816 | 7/1992 | Brown et al. | 417/2 |
| 5,181,910 | 1/1993 | Scanlon | 604/67 |
| 5,221,268 | 6/1993 | Barton et al. | 604/250 |
| 5,244,463 | 9/1993 | Cordner, Jr. et al. | 604/131 |
| 5,256,156 | 10/1993 | Kern et al. | 604/246 |
| 5,256,157 | 10/1993 | Samiotes et al. | 604/246 |
| 5,257,978 | 11/1993 | Haber et al. | 604/250 |
| 5,298,021 | 3/1994 | Sherer | 604/66 |
| 5,304,127 | 4/1994 | Kawahara et al. | 604/65 |

INFUSION PUMP AND METHOD WITH DOSE-RATE CALCULATION

This is a continuation of U.S. application Ser. No. 08/225,753, filed Apr. 11, 1994, now abandoned.

BACKGROUND OF THE INVENTION

The present invention relates to an infusion pump and method for continuously infusing a patient with a drug over a relatively long period of time, and more particularly to an infusion pump and method in which drug dose and rate calculations are performed based on infusion parameters input to the infusion pump by the user.

An infusion pump is used to continuously infuse a patient with a particular drug over a relatively long period of time, such as several hours or days. The drug is infused by the pump from a drug supply, such as a disposable plastic bag containing a predetermined volume and concentration of the drug. The duration of the infusion may necessitate periodic replacement of the drug bag.

An infusion pump may have a number of modes of operation, including a manual mode in which the user of the pump specifies the drug flow rate at which the pump is to infuse the patient and an automatic mode in which the pump may be programmed by the user to calculate the drug flow rate from a plurality of infusion parameters input by the user. The infusion parameters may be the drug dose and dose mode recommended or prescribed by a doctor, such as milligrams per minute, the concentration of the drug contained in the drug bag, and sometimes the weight of the patient. The manner in which some infusion pumps must be programmed in the automatic mode is relatively complicated and time consuming, which can be especially disadvantageous in emergency situations when fast action is required.

Some types of infusion pumps may incorporate a pumping mechanism which may not be able to pump fluids in continuously varying amounts. For example, the pumping mechanism may be able to pump fluid at a plurality of discrete flow rates, the smallest increment of which may be 0.1 milliliters per hour. Thus, in such a conventional pump where the infusion rate is automatically determined from a plurality of infusion parameters input by the user, the calculated infusion rate is typically rounded, for example, to the nearest 0.1 milliliters per hour. As a result of such rounding, the actual drug dose infused to the patient is not exactly equal to the intended drug dose input by the user of the pump, which can be misleading to the user if the actual drug dose is not displayed on the pump. In some cases where the intended dose is relatively small, the discrepancy between the intended dose and the dose actually administered to the patient can be substantial.

SUMMARY OF THE INVENTION

The invention is directed to an infusion pump and method of operating an infusion pump in which the user of the infusion pump is prompted to input a number of infusion parameters, which include a dose mode, a drug dose, the amount of drug contained in the drug container connected to the infusion pump, the volume of the drug in the drug container, and the patient weight if required by the dose mode. After the parameters are input by the user, the infusion pump automatically calculates an infusion rate corresponding to the desired drug dose input by the user and continuously infuses the patient with the drug in accordance with the calculated infusion rate. The invention has a number of different aspects and numerous features and advantages.

In one aspect, the invention is directed to a method of operating an infusion pump in which the user of the infusion pump is prompted to input a plurality of infusion parameters into the infusion pump, including an intended dose of a drug to be administered to a patient. The infusion pump then calculates a drug flow or infusion rate based upon the infusion parameters input by the user and rounds the calculated drug flow rate. The infusion pump then calculates an actual drug dose from the rounded drug flow rate and generates a visual display of the actual drug dose. As a result, the user will be able to inspect the actual drug dose administered to the patient to determine how much it varies from the intended dose.

Another aspect of the invention allows the infusion pump to be programmed while it is infusing the patient, which is advantageous in emergency circumstances since an initial infusion may be quickly started without the need to program the infusion pump with all the infusion parameters and a more precise infusion can be subsequently programmed while the initial infusion is running. In this aspect of the invention, while the patient is being continuously infused with a drug over a first period of time, the user of the infusion pump is prompted to input a plurality of infusion parameters including a dose mode and a drug dose, and a drug infusion rate is calculated based upon the infusion parameters. After the infusion rate is calculated, the patient is continuously infused in accordance with the calculated infusion rate over a second time period.

In a further aspect, the invention is directed to a method of operating an infusion pump which allows the infusion pump to be programmed more quickly and simply by the user. In accordance with this method, the user is prompted to input a plurality of infusion parameters into the infusion pump, one of which is a dose mode that is selectable from a plurality of dose modes including a first dose mode which is based upon the weight of the patient to be infused and a second dose mode which is not based upon the weight of the patient to be infused. After the dose mode is input by the user, the infusion pump automatically determines whether the user input the first dose mode, which requires the patient weight, or the second dose mode, which does not require the patient weight. The infusion pump then prompts the user for the weight of the patient only if the first dose mode was input by the user. The infusion pump then calculates the drug infusion rate based upon the infusion parameters and continuously infuses the patient based upon the calculated infusion rate.

These and other features and advantages of the invention will be apparent to those of ordinary skill in the art in view of the detailed description of the preferred embodiment, which is made with reference to the drawings, a brief description of which is provided below.

DETAILED DESCRIPTION OF THE PREFERRED EMBODIMENT

Figure 1:
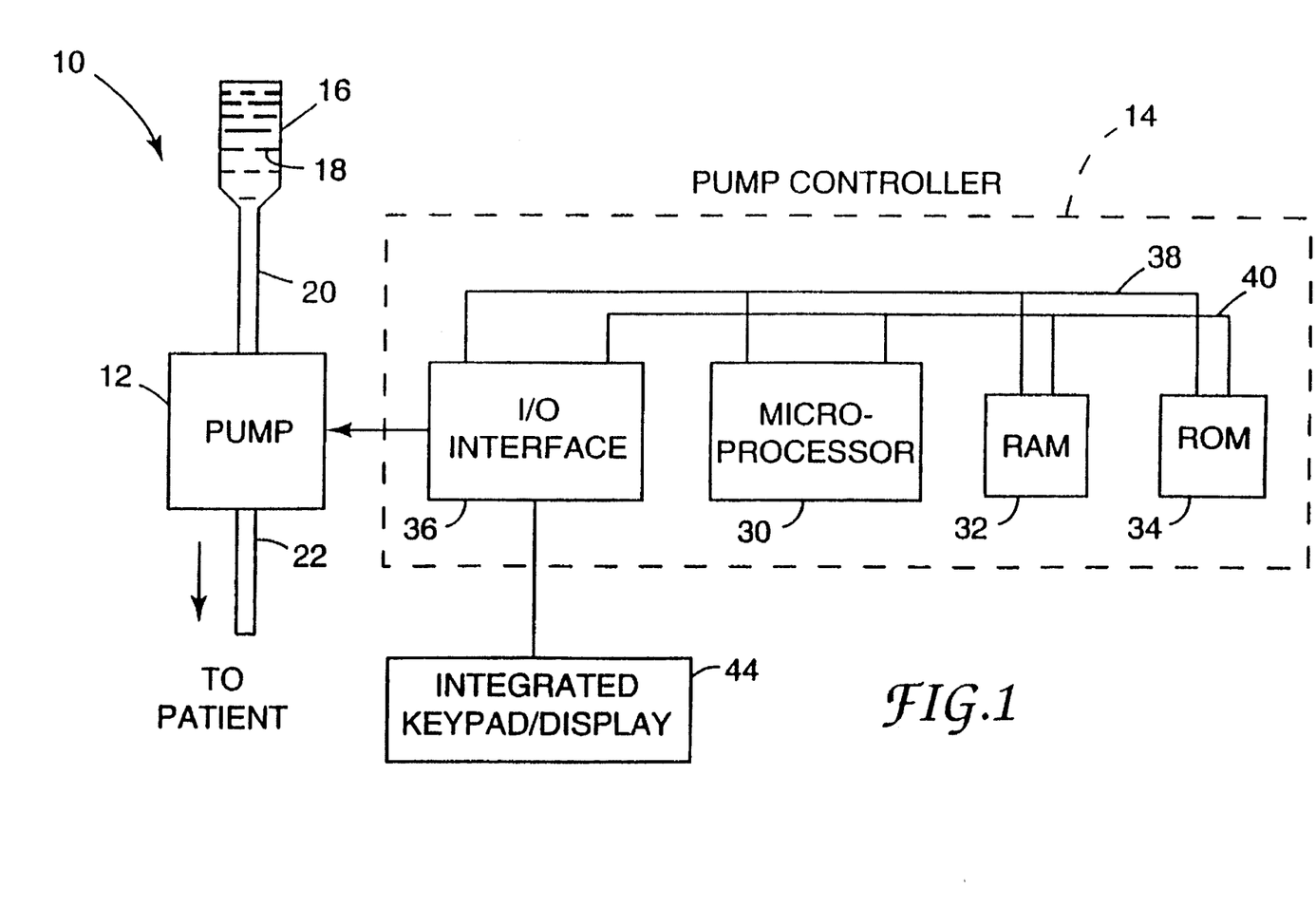
FIG. 1 is a schematic diagram of an embodiment of an infusion pump in accordance with the invention.

A schematic diagram of an embodiment of an infusion pump 10 in accordance with the invention is shown to include a pump 12 electrically connected to and driven by a pump controller 14. The pump 12 is connected to a fluid container 16, such as a disposable plastic bag, which contains a liquid drug 18. The drug 18, which is supplied to the pump 12 via a fluid line 20, is continuously infused over a relatively long period of time, such as several hours or days for example, into a patient by the pump 12 via a fluid line 22, such as an intravenous line, connected to a catheter or other injection means (not shown) connected to the patient. The pump 12 may be a syringe pump or a volumetric pump of the type disclosed in U.S. Pat. No. 4,322,201 to Archibald, the disclosure of which is incorporated herein by reference, but the particular design of the pump 12 is not considered important to the invention.

The pump controller 14 includes a microprocessor 30, a random-access memory (RAM) 32, a read-only memory (ROM) 34, and an input/output (I/O) interface 36, all of which are interconnected via a data bus 38 and an address bus 40. The pump controller 14 may include additional hardware components, such as microprocessors, which relate to other functions and features that are not considered to be pertinent to the invention.

The infusion of the drug 18 into the patient is controlled in accordance with a number of infusion parameters input to the infusion pump 10 by the user of the pump, who is typically a nurse or physician, through an integrated keypad/display 44 connected to the pump controller 14 via the I/O interface 36.

Figure 2:
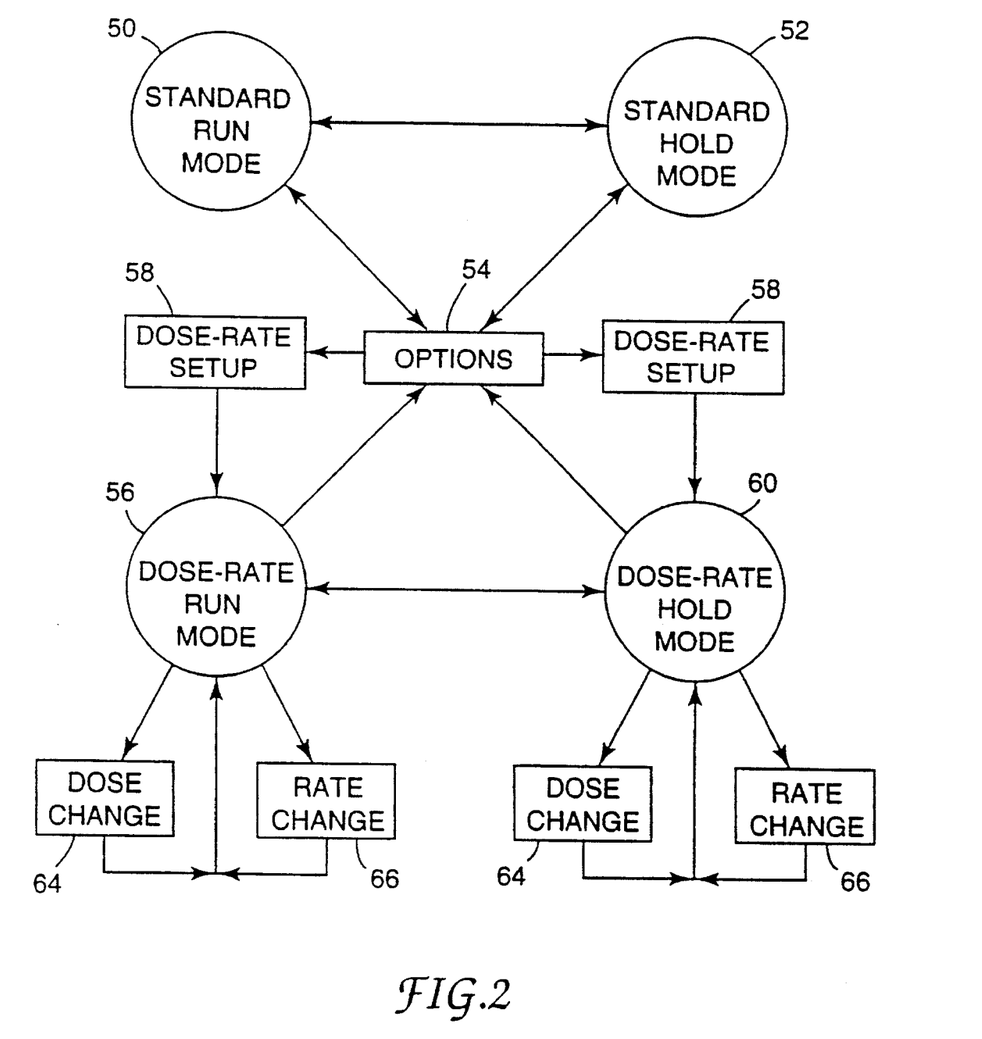
FIG. 2 is a diagram illustrating the overall operation of the infusion pump.

The operation of the infusion pump 10 is controlled by a computer program which is stored in the ROM 34 and run by the microprocessor 30. A diagram of the overall operation of the infusion pump 10 is illustrated in FIG. 2. Referring to FIG. 2, the overall operation of the infusion pump 10 includes a standard run mode 50 and a standard hold mode 52. During the standard run mode 50, the pump 12 causes the patient to be continuously infused with a particular drug flow rate, such as milliliters per hour (ml/hr), which is specified by the user. Use of the standard run mode requires that the user know the particular drug flow rate at which the drug is to be infused. Since the user may know only the dose of the drug to be administered, such as milligrams per hour (mg/hr), and not the corresponding drug flow rate, use of the standard run mode 50 is limited.

If the user wishes to temporarily suspend the drug infusion to the patient, the user may cause the infusion pump 10 to transition to the standard hold mode 52 by pressing a pushbutton or key on the integrated keypad/display 44, such as a "Hold" key. The infusion pump 10 remains in the standard hold mode 52 until instructed by the user, by pressing another key, such as a "Run" key, to transition back to the standard run mode 50. While in the standard hold mode 52, the infusion pump 10 may generate a warning message as a reminder to the user that the drug infusion to the patient has been interrupted.

An options routine 54 may be invoked from either the standard run mode 50 or the standard hold mode 52 to allow the user to cause the infusion pump 10 to operate in a dose-rate run mode 56 via a dose-rate setup routine 58. In the dose-rate run mode 56, the infusion pump 10 infuses the patient with a drug flow rate, such as ml/hr, that was calculated by the infusion pump 10 from a number of infusion parameters input by the user during the dose-rate setup routine 58. The dose-rate run mode 56 is advantageous in that the user does not need to know the flow rate to be administered, which is automatically calculated by the infusion pump 10 from the input infusion parameters.

The infusion pump 10 may operate in a dose-rate hold mode 60 in which the drug infusion to the patient is temporarily suspended. The user may cause the infusion pump 10 to change between the dose-rate run and hold modes 56, 60 via the "Run" and "Hold" keys described above. The dose-rate hold mode 60 may also be entered frown the options 54 via the dose-rate setup routine 58. Although the dose-rate setup routine 58 is shown in two places in FIG. 2, it should be understood that there is only one such routine.

The options routine 54, which may also be invoked from either the dose-rate run mode 56 or the dose-rate hold mode 60, allows the user to cause the infusion pump 10 to operate in additional modes, such as a quick-rate-change mode, a rate-taper mode, and a volume-over-time mode, and to perform certain procedures, such as changing the panel lighting of the keypad/display 44 and performing a battery test. Since these other modes and procedures are not considered pertinent to the invention, they are not described in detail.

The infusion pump 10 may perform a dose-change routine 64 or a rate-change routine 66 from either the dose-rate run mode 56 or the dose-rate hold mode 60. The dose-change routine 64, when invoked from the dose-rate run mode 56, allows the user to input a single infusion parameter consisting of a new drug dose, and the infusion pump 10 automatically calculates and displays a new infusion rate based on the new dose, and infuses the patient at the new rate. When invoked from the dose-rate hold mode 60, the dose-change routine 64 changes the dose in the manner described above, but the new infusion rate is not administered to the patient until the infusion pump 10 transitions from the dose-rate hold mode 60 to the dose-rate run mode 56.

The rate-change routine 66, when invoked from the dose-rate run mode 56, allows the user to input a single infusion parameter consisting of a new drug infusion rate. The infusion pump 10 then automatically calculates a new drug dose based on the new infusion rate, displays the new drug dose to the user, and infuses the patient at the new infusion rate. When invoked from the dose-rate hold mode 60, the rate-change routine 66 displays the new dose and changes the infusion rate in the manner described above, but the new infusion rate is not administered to the patient until the infusion pump 10 transitions from the dose-rate hold mode 60 to the dose-rate run mode 56.

Figure 3A:
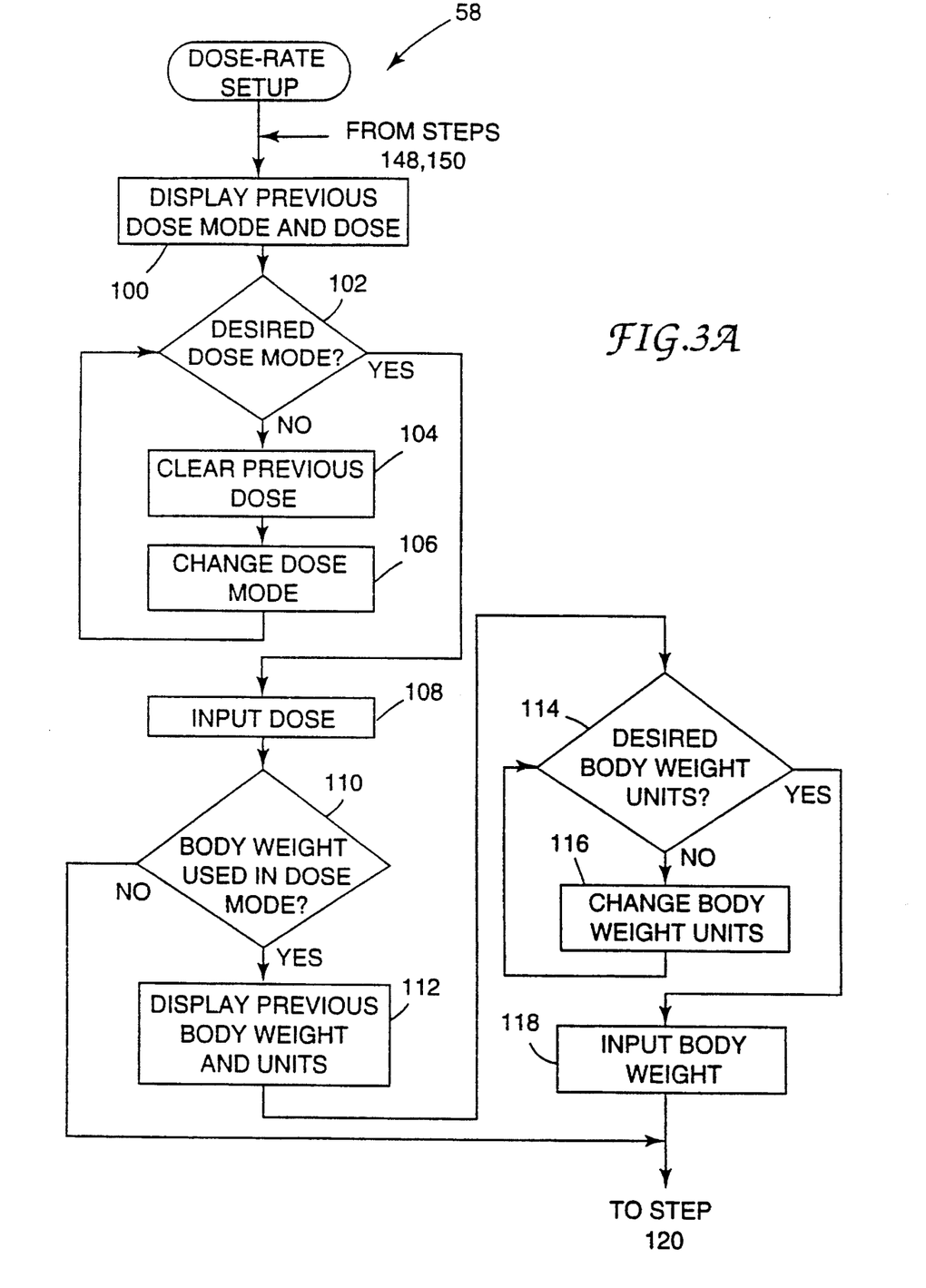
FIGS. 3A–3C illustrate a flowchart of a dose-rate setup routine that is performed during the operation of the infusion pump.
Figure 3B:
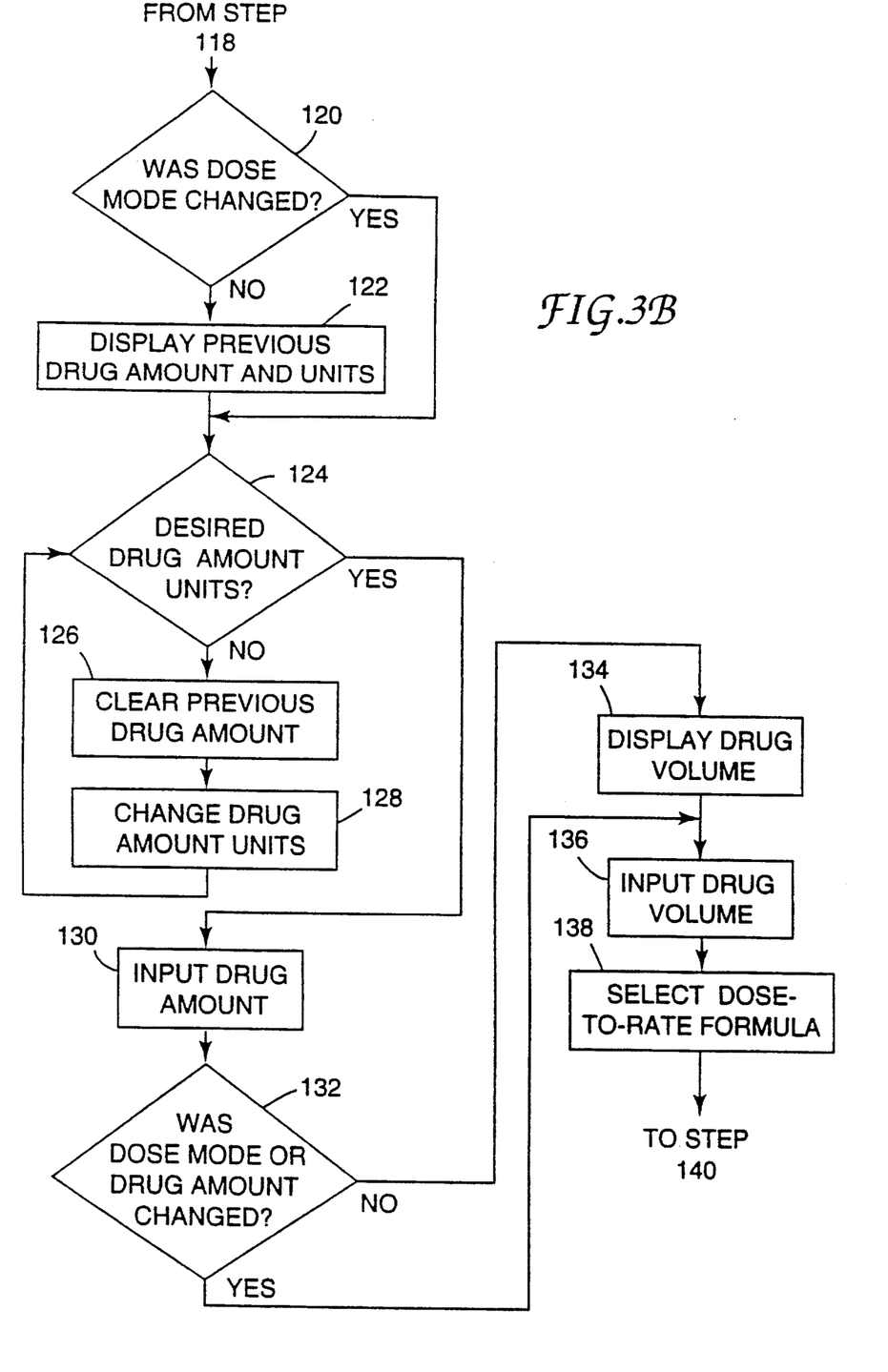
Figure 3C:
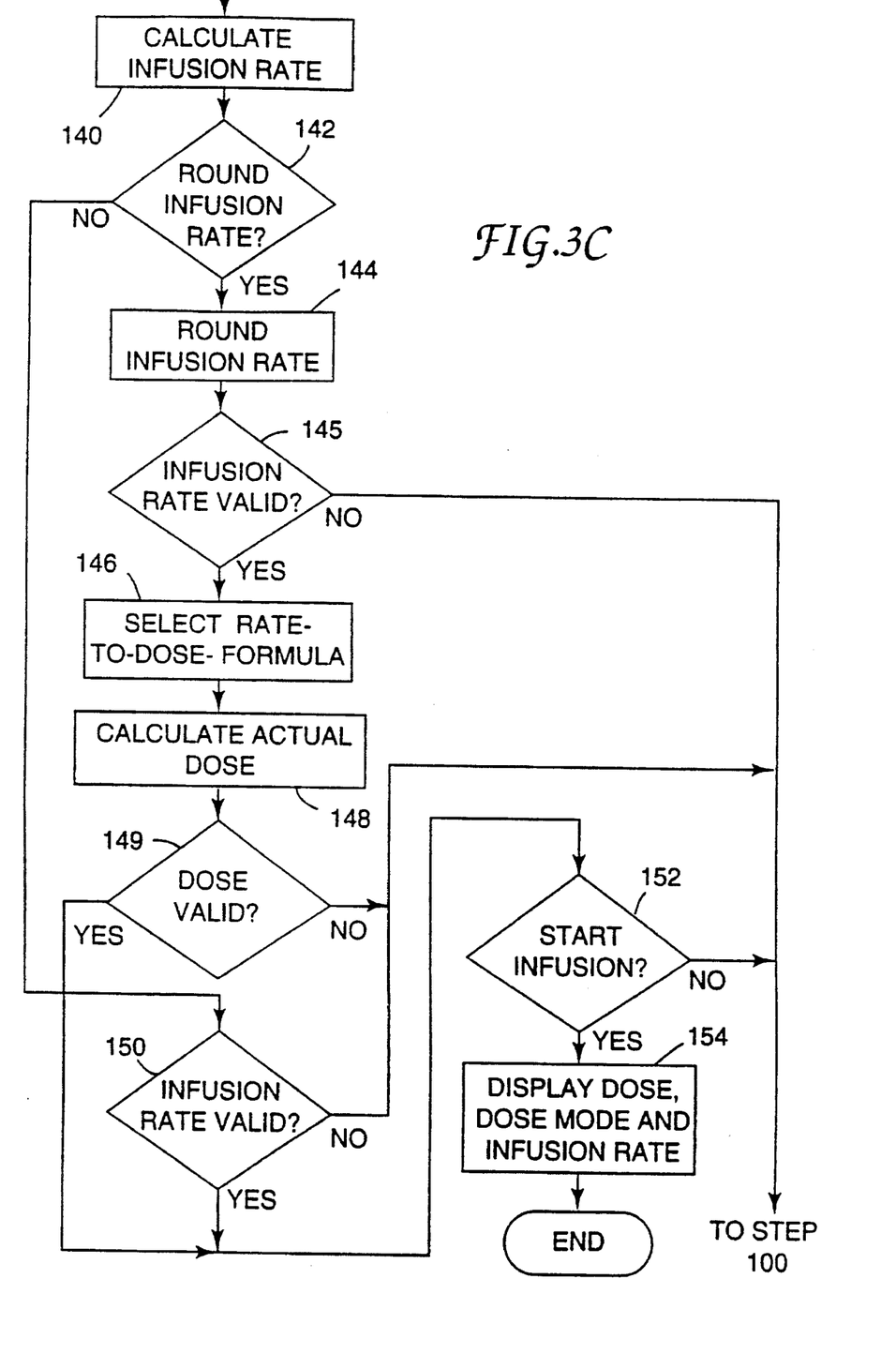

FIGS. 3A–3C illustrate a flowchart of the dose-rate setup routine 58 shown schematically in FIG. 2. Referring to FIG. 3A, at step 100 of the dose-rate setup routine 58, the previous dose mode and drug dose are displayed on the integrated keypad/display 44. The previous dose mode and dose are stored in the RAM 32, at least a portion of which is nonvolatile due to a battery backup (not shown) so that the infusion parameters stored in the RAM 32 can be retrieved later on, even if the electrical power to the infusion pump 10 was turned off.

There are a number of situations in which the same infusion parameters as previously input infusion parameters are used. Typically, infusion is provided to a patient over a relatively long period of time, such as several days, during which the contents of a number of drug containers 16 are emptied. Each time a new container 16 is connected, the same infusion parameters are typically used. In another situation, the infusion pump 10 may be preprogrammed with the appropriate infusion parameters, such as before an operation on a patient, so that the infusion pump 10 can be connected to the patient immediately after the operation without the need to program it at that time.

At step 102, if the dose mode displayed at step 100 is not the dose mode desired by the user, at step 104 the visual representation of the numeric value of the previous dose, such as mg/kg/min, is cleared from the display 44. The infusion pump 10 is programmed to assume that if the dose mode is changed by the user, the numeric value of the dose to be used will be different than that of the previous dose. Since the infusion pump 10 is programmed to allow the user to input a numeric value displayed on the display 44 by pressing an enter key, without having to key in the multi-digit numeric value, clearing the dose value from the display 44 at step 104 forces the user to type in the new dose value.

At step 106, the user may press a key to change the dose mode. The infusion pump 10 has eight possible dose modes: 1) micrograms/kilogram/minute (mcg/kg/min); 2) micrograms/minute (meg/min); 3) milligrams/minute (mg/min); 4) milligrams/hour (mg/hr); 5) units/hour; 6) milligrams/kilogram/hour (mg/kg/hr); 7) micrograms/kilogram/hour (mcg/kg/hr); and 8) milligrams/kilogram/minute (mg/kg/min). The dose modes 1), 6), 7) and 8) are based on the weight of the patient; in these dose modes, the first parameter refers to the amount of the drug to be infused for each kilogram of body weight for each time unit specified by the third parameter. In each of the other four dose modes, the amount of the drug specified by the first parameter is infused for each time unit specified by the second parameter.

The first dose mode that is displayed on the display 44 for selection by the user is the dose mode that was used most recently. If the user indicates that another dose mode is desired, the other dose modes are displayed on the display 44, one at a time, in order of frequency of use, the first dose mode being the one that is most frequently used and the last dose mode being the one that is least frequently used. The user toggles through the dose modes until the desired mode is displayed.

At step 108, the user inputs the drug dose to be provided to the patient. This may be accomplished in two ways. If the dose mode was not changed, the user may select the numeric dose value displayed (at step 100) to be the desired dose value by pressing a single key, such as a "*" key. If the dose mode was changed from the previous dose mode, then the user inputs the numeric value of the dose in the units corresponding to the dose mode. For example, if the dose mode is mcg/min, the user would input the dose value in micrograms/minute.

At step 110, if the current dose mode is one of the four modes based on patient body weight, the routine branches to step 112 where the previous body weight and units, in either pounds or kilograms, are displayed on the display 44. At step 114, if the body weight units displayed are not the units desired by the user, at step 116 the user may change the body weight units. When the desired body weight units are displayed, at step 118 the user inputs the patient body weight either by pressing an enter key which causes the displayed body weight (at step 112) to be input or alternatively, by entering a different body weight.

A second portion of the dose-rate setup routine 58 is illustrated in FIG. 3B. During steps 120–136 of FIG. 3B, the amount of the drug in the container 16 and the fluid volume of the drug in the container 16 are input by the user. The drug amount and the drug fluid volume are normally printed on the container 16, which is typically a plastic bag or a glass bottle. The drug concentration, which is determined by dividing the drug amount by the fluid volume, is not usually printed on the container 16. Since the infusion pump 10 does not require the user to input the drug concentration, there is no need for the user to manually calculate the drug concentration.

Referring to FIG. 3B, at step 120, if the dose mode was not changed at step 106 (FIG. 3A) from the previous dose mode, the numeric value of the previous drug amount and the drug units, such as milligrams, are displayed at step 122. At step 124, if the drug amount units displayed on the display 44 are not the desired units, at step 126 the numeric value of the previous drug amount (that was displayed at step 122) is cleared from the display 44. At step 128, the user selects the desired drug amount units, which may be milligrams, grams, micrograms, or units.

After the desired drug amount traits are selected, at step 130 the user inputs the numeric value of the drug amount in the same units as those selected, such as in milligrams. This can be accomplished in two ways. If the previous drug amount is displayed on the display 44 (and was not cleared during step 126), the user may input this drug amount by pressing a single entry key. If the previous drug amount is not displayed, the user inputs the numeric value of the drug amount.

At step 132, if neither the dose mode nor the numeric value of the drug amount was changed, at step 134 the numeric value of the previous drug volume is displayed on the display 44. At step 136, the user inputs the drug volume either by accepting the numeric value of the displayed drug volume by pressing an enter key, or if no drug volume is displayed, by entering the drug volume. The drug volume is entered in milliliters.

At step 138, the infusion pump 10 automatically selects the proper dose-to-rate formula, based on the infusion parameters input by the user, to calculate the infusion rate (in ml/hr) that the pump 12 will administer to the patient. The proper dose-to-rate formula is selected based upon: 1) the dose mode input by the user and 2) the units (micrograms, milligrams, grams or units) in which the drug amount was input by the user. The dose-to-rate equations for each dose mode are set forth in Table 1 below.

TABLE 1

| DOSE MODE | DOSE-TO-RATE EQUATION |
|---|---|
| mcg/kg/min | a) Rate = (Dose * W * 60 * (1/1000))/(A/V) |
|  | b) Rate = (Dose * W * 60)/(A/V) |
|  | c) Rate = (Dose * W * 60 * (1/1,000,000))/(A/V) |
| mcg/min | a) Rate = (Dose * 60 * (1/1000))/(A/V) |
|  | b) Rate = (Dose * 60)/(A/V) |
|  | c) Rate = (Dose * 60 * (1/1,000,000))/(A/V) |
| mg/min | a) Rate = (Dose * 60)/(A/V) |
|  | b) Rate = (Dose * 60 * 1000)/(A/V) |
|  | c) Rate = (Dose * 60 * (1/1000))/(A/V) |
| mg/hour | a) Rate = Dose/(A/V) |
|  | b) Rate = (Dose * 1000)/(A/V) |
|  | c) Rate = (Dose * (1/1000))/(A/V) |
| units/hour | Rate = Dose/(A/V) |
| mg/kg/hr | a) Rate = (Dose * W)/(A/V) |
|  | b) Rate = (Dose * W * 1000)/(A/V) |
|  | c) Rate = (Dose * W * (1/1000))/(A/V) |
| mcg/kg/hr | a) Rate = (Dose * W * (1/1000))/(A/V) |
|  | b) Rate = (Dose * W)/(A/V) |

TABLE 1-continued

| DOSE MODE | DOSE-TO-RATE EQUATION |
|---|---|
| mg/kg/min | c) Rate = (Dose * W * (1/1,000,000))/(A/V)<br>a) Rate = (Dose * W * 60)/(A/V)<br>b) Rate = (Dose * W * 60 * 1000)/(A/V)<br>c) Rate = (Dose * W * 60 * (1/1000))/(A/V) |

In the above dose-to-rate equations, Rate is the infusion rate (in ml/hr) to be delivered to the patient by the pump 12, Dose is the drug dose input by the user, A is the drug amount input by the user, V is the drug volume input by the user (A/V represents the drug concentration), and W is the patient's body weight in kilograms, which is either the numeric value input by the user or, if the body weight was input in pounds, was calculated by the infusion pump 10 with the kg/lbs conversion factor. The dose-to-rate equations listed in category a) above are used when the drug amount A was input by the user in milligrams; the category b) dose-to-rate equations are used when the drug amount A was input in micrograms; and the category c) dose-to-rate equations are used when the drug amount A was input in grams.

Referring to FIG. 3C, after the proper dose-to-rate equation is selected, at step 140 the infusion rate is calculated based on the infusion parameters input by the user. The infusion rate calculated at step 140 may have to be rounded since the flow rates which the pump 12 is capable of delivering may not be continuously variable. For example, the pump 12 may be capable of delivering discrete flow rates which incrementally vary by 0.1 ml/hr. In that case, a flow rate calculated to be 0.105 ml/hr would be rounded to 0.1 ml/hr.

One rounding scheme that may be used is to round flow rates in different ways, depending on the magnitude of the flow rate. For flow rates less than 0.1 ml/hr, no rounding is performed. For flow rates between 0.1 ml/hr and 100 ml/hr, a flow rate between xx.x01 and xx.x49 is rounded to xx.x and a flow rate between xx.x50 and xx.x99 is rounded to xx.(x+1). For example, if the calculated flow rate is 23.337 ml/hr, the rate would be rounded to 23.3 ml/hr. For flow rates equal to or greater than 100 ml/hr, a flow rate between xxx.01 and xxx.49 is rounded to xxx. and a flow rate between xxx.50 and xxx.99 is rounded to xxx+1. Other rounding schemes could be used. At step 142, if the infusion rate needs to be rounded, the program branches to step 144 where the infusion rate is rounded.

At step 145, the infusion pump 10 determines if the rounded infusion rate is valid by checking to determine whether it falls within a predetermined numeric range, which represents the range of flow rates which the pump 12 is capable of delivering to the patient. For example, the permissible flow rate range may have a minimum flow rate of 0.1 ml/hr and a maximum flow rate of 999 ml/hr. If the infusion rate does not fall within the permissible range, the infusion rate is not considered to be valid, a message to that effect is displayed on the display 44, and the routine branches back to step 100 where the user may input different infusion parameters to obtain a valid infusion rate.

If the infusion rate was rounded at step 144, the actual drug dose administered to the patient will not exactly equal the intended dose input by the user. To inform the user of the actual dose to be delivered, the infusion pump 10 calculates the actual dose frown the rounded infusion rate. This is accomplished by first selecting a proper rate-to-dose equation at step 146 to convert the rounded infusion rate back to a corresponding dose, and then calculating the dose in accordance with the selected rate-to-dose equation at step 148. At step 146, the infusion pump 10 automatically selects the proper rate-to-dose equation to calculate the actual dose that will be administered to the patient.

The proper rate-to-dose equation is selected based upon: 1) the dose mode selected by the user, and 2) the units (micrograms, milligrams, grams or units) in which the drug amount was entered by the user. The rate-to-dose equations for each dose mode are set forth in Table 2 below.

TABLE 2

| DOSE MODE | RATE-TO-DOSE EQUATION |
|---|---|
| mcg/kg/min | a) Dose = (Rate * (A/V) * 1000)/(W * 60)<br>b) Dose = (Rate * (A/V))/(W * 60)<br>c) Dose = (Rate * (A/V) * 1,000,000)/(W * 60) |
| mcg/min | a) Dose = (Rate * (A/V) * 1000)/60<br>b) Dose = (Rate * (A/V))/60<br>c) Dose = (Rate * (A/V) * 1,000,000)/60 |
| mg/min | a) Dose = (Rate * (A/V))/60<br>b) Dose = (Rate * (A/V))/(60 * 1000)<br>c) Dose = (Rate * (A/V) * 1000)/60 |
| mg/hour | a) Dose = Rate * (A/V)<br>b) Dose = (Rate * (A/V))/1000<br>c) Dose = (Rate * (A/V) * 1000) |
| units/hour | Dose = Rate * (A/V) |
| mg/kg/hr | a) Dose = (Rate * (A/V))/W<br>b) Dose = (Rate * (A/V))/(1000 * W)<br>c) Dose = (Rate * (A/V) * 1000)/W |
| mcg/kg/hr | a) Dose = (Rate * (A/V) * 1000)/W<br>b) Dose = (Rate * (A/V))/W<br>c) Dose = (Rate * (A/V) * 1,000,000)/W |
| mg/kg/min | a) Dose = (Rate * (A/V))/(W * 60)<br>b) Dose = (Rate * (A/V))/(W * 60 * 1000)<br>c) Dose = (Rate * (A/V) * 1000)/(W * 60) |

The variables set forth in the above rate-to-dose equations are the same as those set forth in the dose-to-rate equations of Table 1, except that Rate represents the rounded infusion rate determined at step 144 and Dose represents the actual drug dose to be administered to the patient. The rate-to-dose equations listed in category a) above are used when the drug amount A was input by the user in milligrams; the category b) rate-to-dose equations are used when the drug amount A was entered in micrograms; and the category c) rate-to-dose equations are used when the drug amount A was input in grams.

At step 149, the infusion pump 10 determines if the dose calculated at step 148 is valid by checking to determine whether it falls within a permissible dose range between a minimum dose and a maximum dose. If the dose does not fall within the permissible range, the dose calculated at step 148 is not considered to be valid, a message to that effect is displayed on the display 44, and the routine branches back to step 100 where the user may input different infusion parameters to obtain a valid dose.

At step 150, which is the same as step 145 described above and is preformed if the infusion rate was not to be rounded as determined at step 142, the infusion pump 10 determines if the infusion rate calculated at step 140 is valid. If it is not, a message to that effect is displayed on the display 44, and the routine branches back to step 100 where the user may input different infusion parameters to obtain a valid infusion rate.

At step 152, the user may decide either to begin the infusion or to review the infusion parameters that were entered by running through the dose-rate setup routine 58 again. In the latter case, the program branches to step 100 (FIG. 3A). If the user elected to start the infusion, at step 154 the dose, the dose mode, and the infusion rate (in ml/hr) are displayed on the display 44. The dose that is displayed is the actual dose calculated at step 148 if the infusion rate was rounded, or the dose input by the user if the infusion rate was not rounded.

The set-up routine 58 assumes that the volume of the drug to be infused over the relatively long infusion period is equal to the fluid contents of the drug container 16. This assumption, which can be changed by the user, saves time in programming the pump with the infusion parameters.

Referring back to FIG. 2, if the dose-rate setup routine 58 was invoked through the options routine 54 when the infusion pump 10 was in one of the run modes 50, 56, after step 154 (FIG. 3C) the pump 12 will begin the infusion to the patient at the infusion rate displayed at step 154 (when the user presses the "Run" key), and the current infusion pump state will be the dose-rate run mode 56. If the dose-rate setup routine 58 was invoked through the options routine 54 when the infusion pump 10 was in one of the hold modes 52, 60, after step 154 (FIG. 3C), the pump 12 will not immediately begin infusing at the infusion rate displayed at step 154, and the infusion pump 10 will be in the dose-rate hold mode 60. To begin infusing at the infusion rate displayed at step 154, the user would press the "Run" key, which would cause a transition frown the dose-rate hold mode 60 to the dose-rate run mode 56.

It should be appreciated that the set-up routine 58 allows the infusion pump 10 to be programmed in a very quick and efficient manner, particularly when the infusion pump 10 has been programmed once. For example, after the infusion pump 10 has been initially programed, it can be reprogrammed (assuming the infusion parameters do not change) in accordance with the flowchart of FIGS. 3A–3C by making three keystrokes if patient body weight is not used (at steps 108, 130, 136), or by making four keystrokes if patient body weight is used (at steps 108, 118, 130, 136).

Figure 4:
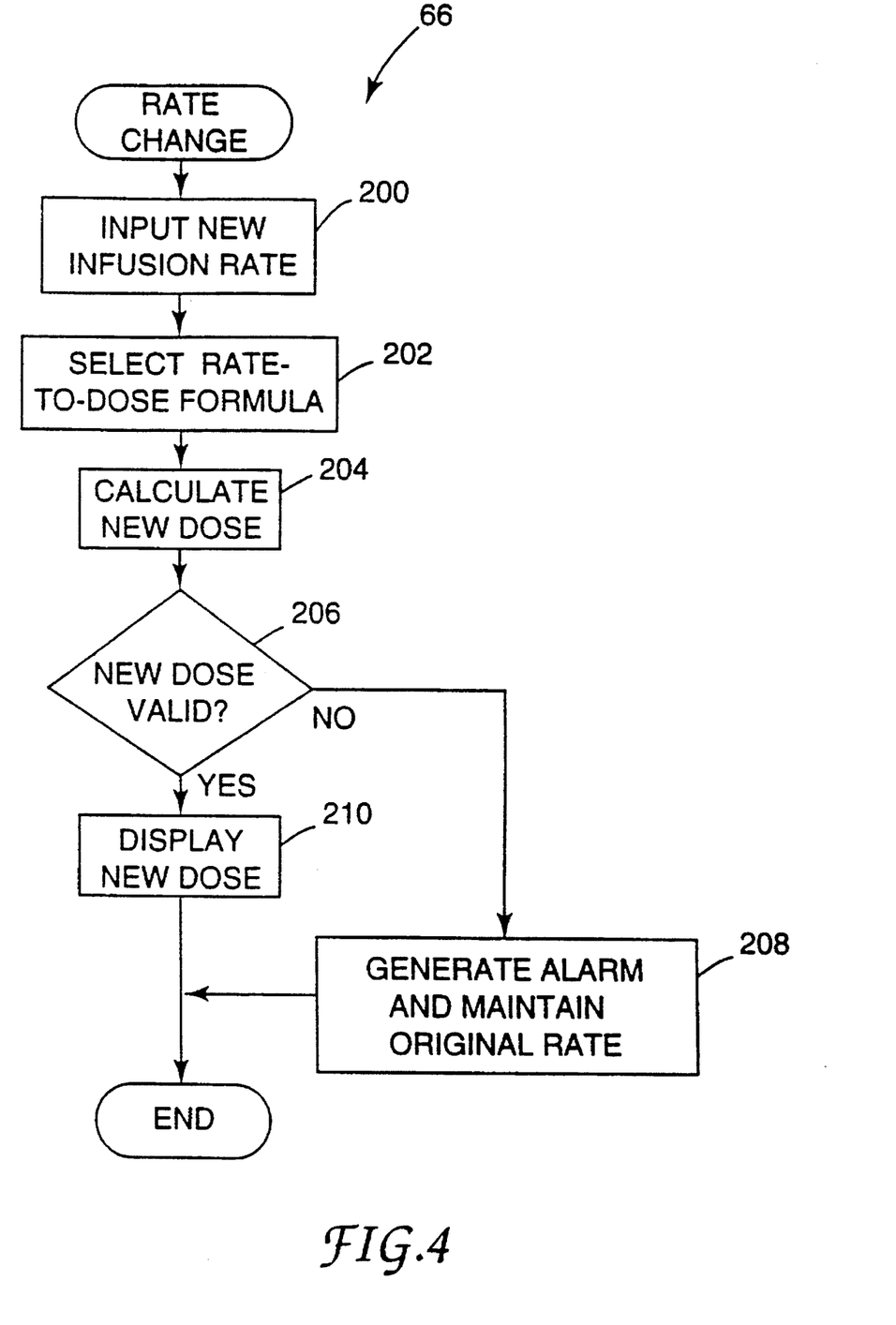
FIG. 4 is a flowchart of a rate-change routine that may be performed during operation of the infusion pump.

FIG. 4 is a flowchart of the rate-change routine 66 shown schematically in FIG. 2. Referring to FIG. 4, the routine begins at step 200 where the user inputs a new infusion rate. At step 202, the proper rate-to-dose formula is selected from Table 2 in accordance with the current dose mode and the units in which the drug amount was input. At step 204, the dose corresponding to the new infusion rate is calculated using the rate-to-dose formula selected in step 202, the new infusion rate input at step 200, and the other current infusion parameters (drug amount A, drug volume V and weight W if necessary), which are stored in the nonvolatile RAM 32. At step 206, the infusion pump 10 determines whether the new dose calculated at step 204 is within a valid dose range having a minimum dose value and a maximum dose value. If the dose is not within the range, the program branches to step 208 where an alarm message is generated and displayed on the display 44 to indicate that the new dose is not valid, and the previous dose is maintained. If the new dose was valid, at step 210 the new dose is displayed on the display 44.

Referring to FIG. 2, if the rate-change routine 66 was invoked from the dose-rate run mode 56, at the completion of the step 210 (FIG. 4) the pump 12 will infuse the patient at the new infusion rate (when the user presses the "Run" key). If the new dose was invalid as determined at step 208, the pump 12 will continue to infuse the patient at the previous infusion rate.

If the rate-change routine 66 was invoked from the dose-rate hold mode 60, the pump 12 will not immediately begin infusing (at either the new rate in case the new dose is valid or the previous rate in case the new dose was invalid). To begin infusing, the user would press the "Run" key, which would cause a transition from the dose-rate hold mode 60 to the dose-rate run mode 56.

Figure 5:
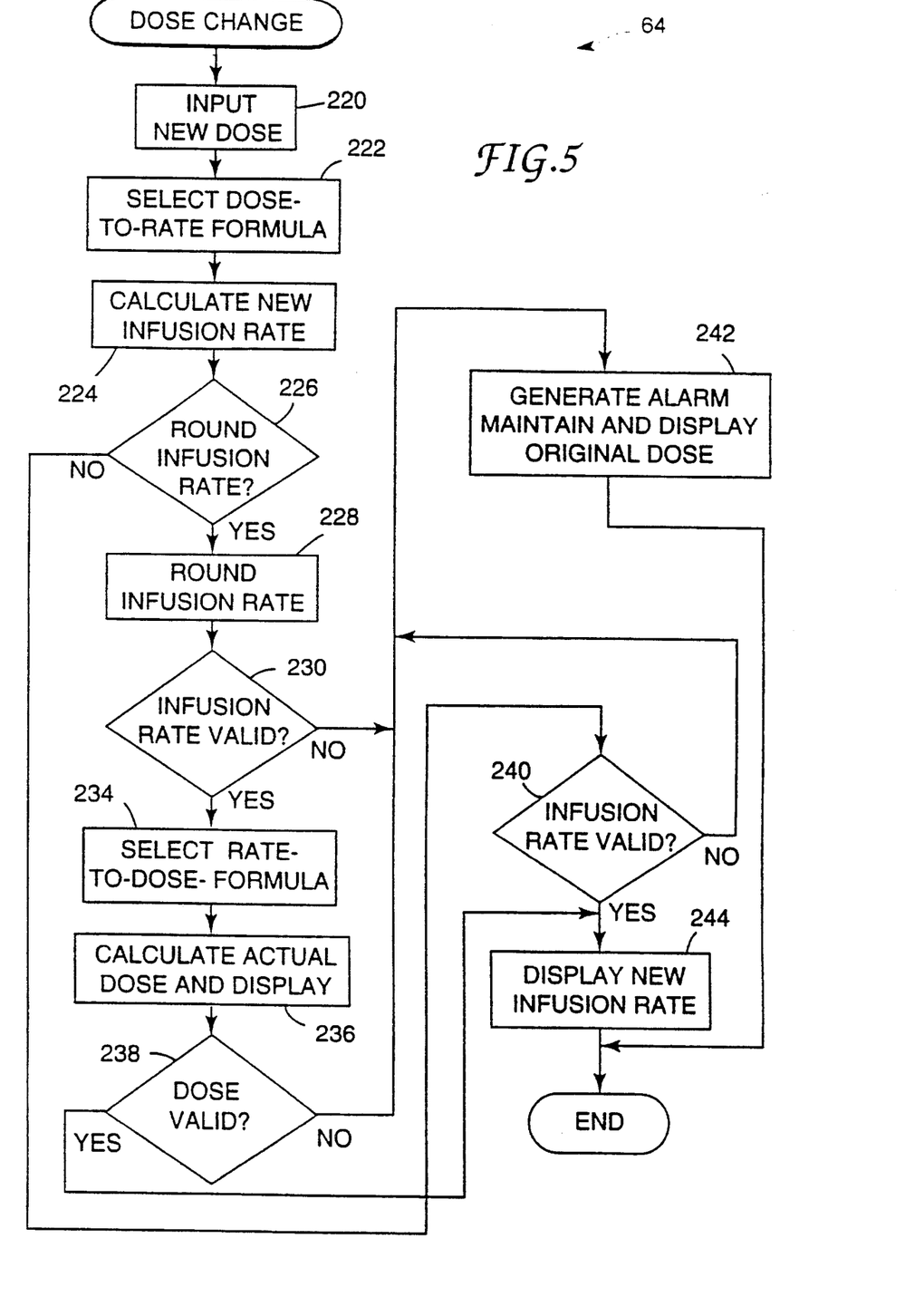
FIG. 5 is a flowchart of a dose-change routine that may be performed during operation of the infusion pump.

FIG. 5 is a flowchart of the dose-change routine 64 shown schematically in FIG. 2. Referring to FIG. 5, the routine begins at step 220 where the user inputs a new drug dose. At step 222, the proper dose-to-rate formula is selected from Table 1 in accordance with the current dose mode and the units in which the drug amount was input. At step 224, the infusion rate corresponding to the new dose value is calculated using the dose-to-rate formula selected in step 222, the new dose value input at step 220, and the other current infusion parameters (drug amount A, drug volume V and weight W if necessary), which are stored in the nonvolatile RAM 32. Since steps 226–238, which round the new infusion rate if necessary and calculate the actual dose to be infused to the patient, are analogous to steps 142–149 of FIG. 3C, the description of such steps is not repeated.

At step 240, which is preformed if the infusion rate was not to be rounded as determined at step 226, the infusion pump 10 determines whether the new infusion rate calculated at step 224 is within a permissible infusion rate range having a minimum infusion rate and a maximum infusion rate. If the infusion rate is not within the range, the program branches to step 242 where an alarm message is generated and displayed on the display 44, the previous infusion rate is maintained, and the original dose is displayed. If the new infusion rate was valid, at step 244 the new infusion rate is displayed on the display 44.

Referring to FIG. 2, if the dose-change routine 64 was invoked from the dose-rate run mode 56, at the completion of the step 244 (FIG. 5) the pump 12 will infuse the patient at the new infusion rate corresponding to the new dose (when the user presses the "Run" key). If the new infusion rate was invalid as determined at either of steps 230, 240 or if the dose was invalid as determined at step 238, the pump 12 will continue to infuse the patient at the previous infusion rate.

If the dose-change routine 64 was invoked from the dose-rate hold mode 60, the pump 12 will not immediately begin infusing (at either the new rate if the new rate is valid or the previous rate if the new rate or dose was invalid). To begin infusing, the user would press the "Run" key, which would cause a transition from the dose-rate hold mode 60 to the dose-rate run mode 56.

Numerous modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A method of operating an infusion pump comprising the steps of:

(a) prompting a user of the infusion pump to input a plurality of infusion parameters into the infusion pump, said plurality of infusion parameters including an intended drug dose of a drug to be administered to a patient;

(b) calculating a drug flow rate based upon said plurality of infusion parameters input by the user during said step (a);

(c) rounding said drug flow rate calculated in said step (b) to generate a rounded drug flow rate;

(d) calculating an actual drug dose from said rounded drug flow rate, said actual drug dose representing the actual drug dose to be infused to the patient; and (e) generating a visual display of said actual drug dose to allow the user to compare said actual drug dose with said intended drug dose.

2. A method as defined in claim 1 additionally comprising the step of (f) continuously infusing the patient with said drug according to said rounded drug flow rate.

3. A method as defined in claim 1 wherein said step (a) additionally comprises the steps of:

(a1) prompting the user to input a dose mode into the infusion pump;

(a2) prompting the user to input a drug amount into the infusion pump; and (a3) prompting the user to input a drug volume into the infusion pump.

4. A method as defined in claim 3 wherein said step (a) additionally comprises the step of (a4) prompting the user to input the weight of the patient into the infusion pump.

5. A method as defined in claim 1 wherein said step (a) additionally comprises the steps of:

(a1) prompting the user to input a dose mode being selectable frown a plurality of dose modes including a first dose mode being micrograms/kilogram/minute, a second dose mode being micrograms/minute, a third dose mode being milligrams/minute, and a fourth dose mode being milligrams/hour;

(a2) prompting the user to input a drug amount into the infusion pump; and (a3) prompting the user to input a drug volume into the infusion pump.

6. A method as defined in claim 5 additionally comprising the step of (f) infusing said drug into the patient from a drug container, wherein said drug volume is the fluid volume of said drug in said drug container and said drug amount is the amount of said drug in said drug container.

7. A method as defined in claim 1 wherein said step (a) is performed while the patient is being infused with said drug.

8. A method as defined in claim 1 wherein said step (a) additionally comprises the steps of:

(a1) prompting the user of the infusion pump to input a dose mode selectable from a plurality of dose modes including a first dose mode which is based upon the weight of the patient to be infused by the infusion pump and a second dose mode which is not based upon the weight of the patient to be infused by the infusion pump;

(a2) determining whether the user input said first dose mode to the infusion pump or said second dose mode to the infusion pump; and (a3) prompting the user for the weight of the patient only if the user input said first dose mode.

9. An apparatus having a memory which contains data generated by the method of claim 1.

10. A method of operating an infusion pump comprising the steps of:

(a) continuously infusing a patient with a drug over a first period of time via an infusion pump;

(b) prompting a user of the infusion pump to input a plurality of infusion parameters into the infusion pump during said step (a) while the patient is being continuously infused with said drug, said step (b) comprising the steps of:

(b1) first prompting the user to input a dose mode; and (b2) after said step (b1), prompting the user to input a drug dose;

(c) calculating a drug flow rate based upon said plurality of infusion parameters input by the user during said step (b); and (d) continuously infusing the patient with said drug over a second period of time based upon said drug flow rate calculated in said step (c).

11. A method as defined in claim 10 wherein said step (c) is performed while the patient is being continuously infused with said drug during said step (a).

12. A method as defined in claim 10 additionally comprising the step of (e) rounding said drug flow rate calculated in said step (c) to generate a rounded drug flow rate and wherein said flow rate infused to the patient during said step (d) is based on said rounded drug flow rate.

13. A method as defined in claim 12 additionally comprising the steps of:

(f) calculating an actual drug dose from said rounded drug flow rate, said actual drug dose representing the actual drug dose to be infused to the patient; and (g) generating a visual display of said actual drug dose.

14. A method as defined in claim 10 wherein said step (b) comprises the steps of:

(b3) prompting the user to input a drug amount into the infusion pump; and (b4) prompting the user to input a drug volume into the infusion pump.

15. A method as defined in claim 14 wherein said drug is infused into the patient from a drug container and wherein said drug volume is the fluid volume of said drug in said drug container and said drug amount is the amount of said drug in said drug container.

16. A method as defined in claim 14 wherein said step (b) additionally comprises the step of (b5) prompting the user to input the weight of the patient into the infusion pump.

17. A method as defined in claim 10 wherein said dose mode is selectable from a plurality of dose modes including a first dose mode being micrograms/kilogram/minute, a second dose mode being micrograins/minute, a third dose mode being milligrams/minute, and a fourth dose mode being milligrams/hour, said step (b) additionally comprising the steps of:

(b3) prompting the user to input a drug amount into the infusion pump; and (b4) prompting the user to input a drug volume into the infusion pump.

18. A method as defined in claim 10 wherein said dose mode is selectable from a plurality of dose modes including a first dose mode which is based upon the weight of the patient to be infused by the infusion pump and a second dose mode which is not based upon the weight of the patient to be infused by the infusion pump, said step (b) additionally comprising the steps of:

(b3) determining whether the user input said first dose mode to the infusion pump or said second dose mode to the infusion pump; and (b4) prompting the user for the weight of the patient only if the user input said first dose mode.

19. A method of operating an infusion pump comprising the steps of:

(a) prompting a user of the infusion pump to input a plurality of infusion parameters into the infusion pump, said plurality of infusion parameters including a dose mode being selectable from a plurality of dose nodes including a first dose mode which is based upon the weight of a patient to be infused by the infusion pump and a second dose mode which is not based upon the weight of a patient to be infused by the infusion pump;

(b) determining whether the user input said first dose mode to the infusion pump or said second dose mode to the infusion pump;

(c) prompting the user for the weight of the patient only if the user input said first dose mode;

(d) calculating a drug flow rate based upon said plurality of infusion parameters input by the user; and (e) continuously infusing the patient with said drug over a period of time based upon said drug flow rate calculated in said step (d).

20. A method as defined in claim 19 wherein said step (a) additionally comprises the steps of:

(a1) prompting the user to input a drug dose into the infusion pump;

(a2) prompting the user to input a drug amount into the infusion pump; and (a3) prompting the user to input a drug volume into the infusion pump.

21. A method as defined in claim 19 wherein said plurality of dose modes include a first dose mode being micrograms/kilogram/minute, a second dose mode being micrograms/minute, a third dose mode being milligrams/minute, and a fourth dose mode being milligrams/hour, said step (a) additionally comprising the steps of:

(a1) prompting the user to input a drug dose into the infusion pump;

(a2) prompting the user to input a drug amount into the infusion pump; and (a3) prompting the user to input a drug volume into the infusion pump.

22. A method as defined in claim 21 wherein said drug is infused into the patient from a drug container and wherein said drug volume is the fluid volume of said drug in said drug container and said drug amount is the amount of said drug in said drug container.

23. A method as defined in claim 19 additionally comprising the step of (f) rounding said drug flow rate calculated in said step (d) to generate a rounded drug flow rate and wherein said flow rate infused to the patient during said step (e) is based on said rounded drug flow rate.

24. A method as defined in claim 19 additionally comprising the steps of:

(f) calculating an actual drug dose from said drug flow rate calculated in said step (d), said actual drug dose representing the actual drug dose to be infused to the patient; and (g) generating a visual display of said actual drug dose.

25. A method as defined in claim 19 wherein said step (a) is performed while the patient is being infused with said drug.

26. A method as defined in claim 19 wherein said first dose mode is selected from the group of dose modes consisting of micrograms/kilogram/minute, milligrams/kilogram/hour, micrograms/kilogram/hour, and milligrams/kilogram/minute and wherein said second dose mode is selected from the group of dose modes consisting of micrograms/minute, milligrams/minute, milligrams/hour, and units/hour.

27. An infusion pump for the continuous infusion of a drug from a drug source into a patient over a period of time, said infusion pump comprising:

pump means for continuously infusing the patient with the drug over a first period of time;

means for prompting a user of said infusion pump to input a dose mode to said infusion pump while the patient is being infused with the drug by said pump means;

means for prompting the user to input an intended drug dose to said infusion pump while the patient is being infused with the drug by said pump means;

means for prompting the user to input a drug amount to said infusion pump while the patient is being infused with the drug by said pump means;

means for prompting the user to input a drug volume to said infusion pump while the patient is being infused with the drug by said pump means;

means for determining whether the user input a dose mode requiring the body weight of the patient;

means for prompting the user to input the body weight of the patient to said infusion pump only if the user selected a dose mode based on the body weight of the patient;

means for determining a drug infusion rate based upon said dose mode, said drug dose, said drug amount, and said drug volume input by the user;

means for rounding said drug infusion rate to generate a rounded drug infusion rate;

means for calculating an actual drug dose from said rounded drug infusion rate, said actual drug dose representing the actual drug dose to be infused to the patient over a second period of time; and display means for generating a visual display of said actual drug dose to allow the user to compare said actual drug dose with said intended drug dose, said pumping means infusing the patient with the drug in accordance with said drug infusion rate over said second period of time.

28. An infusion pump, comprising:

means for prompting a user of the infusion pump to input a plurality of infusion parameters into the infusion pump, said plurality of infusion parameters including an intended drug dose of a drug to be administered to a patient;

means for calculating a drug flow rate based upon said plurality of infusion parameters input by the user;

means for rounding said drug flow rate calculated by said calculation means to generate a rounded drug flow rate;

means for calculating an actual drug dose from said rounded drug flow rate, said actual drug dose representing the actual drug dose to be infused to the patient; and means for generating a visual display of said actual drug dose to allow the user to compare said actual drug dose with said intended drug dose.

29. An infusion pump as defined in claim 28 additionally comprising means for continuously infusing the patient with said drug according to said rounded drug flow rate.

30. An infusion pump as defined in claim 28 wherein said prompting means comprises:

means for prompting the user to input a dose mode into the infusion pump;

means for prompting the user to input a drug amount into the infusion pump; and means for prompting the user to input a drug volume into the infusion pump.

31. An infusion pump as define in claim 30 wherein said prompting means additionally comprises means for prompting the user to input the weight of the patient into the infusion pump.

32. An infusion pump as defined in claim 28 wherein said prompting means additionally comprises:

means for prompting the user to input a dose mode being selectable from a plurality of dose modes including a first dose mode being micrograms/kilogram/minute, a second dose mode being micrograms/minute, a third dose mode being milligrams/minute, and a fourth dose mode being milligrams/hour;

means for prompting the user to input a drug amount into the infusion pump; and means for prompting the user to input a drug volume into the infusion pump.

33. An infusion pump as defined in claim 28 wherein said prompting means additionally comprises:

means for prompting the user of the infusion pump to input a dose mode selectable from a plurality of dose modes including a first dose mode which is based upon the weight of the patient to be infused by the infusion pump and a second dose mode which is not based upon the weight of the patient to be infused by the infusion pump;

means for determining whether the user input said first dose mode to the infusion pump or said second dose mode to the infusion pump; and means for prompting the user for the weight of the patient only if the user input said first dose mode.

34. An infusion pump, comprising:

means for continuously infusing a patient with a drug over a first period of time;

means for prompting a user of the infusion pump to input a plurality of infusion parameters into the infusion pump while the patient is being continuously infused with said drug, said prompting means comprising:
means for prompting the user to input a dose mode; and
means for prompting the user to input a drug dose after said dose mode is input;

means for calculating a drug flow rate based upon said plurality of infusion parameters input by the user; and means for continuously infusing the patient with said drug over a second period of time based upon said drug flow rate calculated by said calculating means.

35. An infusion pump as defined in claim 34 wherein said means for continuously infusing the patient comprises means for continuously infusing the patient with said drug over a second period of time based upon said drug flow rate calculated by said calculating means.

36. An infusion pump as defined in claim 34 additionally comprising means for rounding said drug flow rate calculated by said calculating means to generate a rounded drug flow rate and wherein said means for continuously infusing the patient comprises means for continuously infusing the patient with said drug over a second period of time based upon said rounded drug flow rate calculated by said rounding means.

37. An infusion pump as defined in claim 36 additionally comprising:

means for calculating an actual drug dose from said rounded drug flow rate, said actual drug dose representing the actual drug dose to be infused to the patient; and means for generating a visual display of said actual drug dose.

38. An infusion pump as defined in claim 34 wherein said means for prompting the user to input a dose mode comprises means for prompting the user to input a dose mode selectable from a plurality of dose modes including a first dose mode being micrograms/kilogram/minute, a second dose mode being micrograms/minute, a third dose mode being milligrams/minute, and a fourth dose mode being milligrams/hour, said prompting means additionally comprising:

means for prompting the user to input a drug amount into the infusion pump; and means for prompting the user to input a drug volume into the infusion pump.

39. An infusion pump as defined in claim 34 wherein said means for prompting the user to input a dose mode comprises means for prompting the user to input a dose mode selectable from a plurality of dose modes including a first dose mode which is based upon the weight of the patient to be infused by the infusion pump and a second dose mode which is not based upon the weight of the patient to be infused by the infusion pump, the infusion pump additionally comprising:

means for determining whether the user input said first dose mode to the infusion pump or said second dose mode to the infusion pump; and means for prompting the user for the weight of the patient only if the user input said first dose mode.

40. An infusion pump, comprising:

means for prompting a user of the infusion pump to input a plurality of infusion parameters into the infusion pump, said plurality of infusion parameters including a dose mode being selectable from a plurality of dose modes including a first dose mode which is based upon the weight of a patient to be infused by the infusion pump and a second dose mode which is not based upon the weight of a patient to be infused by the infusion pump;

means for determining whether the user input said first dose mode to the infusion pump or said second dose mode to the infusion pump;

means for prompting the user for the weight of the patient only if the user input said first dose mode;

means for calculating a drug flow rate based upon said plurality of infusion parameters input by the user; and means for continuously infusing the patient with said drug over a period of time based upon said drug flow rate calculated by said calculating means.

41. An infusion pump as defined in claim 40 wherein said means for continuously infusing the patient with said drug comprises means for continuously infusing the patient with said drug from a drug container over a period of time based upon said drug flow rate calculated by said calculating means and wherein said prompting means additionally comprises:

means for prompting the user to input a drug amount into the infusion pump, said drug amount being the amount of said drug in said drug container; and means for prompting the user to input a drug volume into the infusion pump, said drug volume being the fluid volume of said drug in said drug container.

42. An infusion pump as defined in claim 40 additionally comprising means for rounding said drug flow rate calculated by said calculating means to generate a rounded drug flow rate and wherein said means for continuously infusing the patient comprises means for continuously infusing the patient with said drug based upon said rounded drug flow rate calculated by said rounding means.

43. An infusion pump as defined in claim 40 additionally comprising:

means for calculating an actual drug dose from said rounded drug flow rate, said actual drug dose representing the actual drug dose to be infused to the patient; and means for generating a visual display of said actual drug dose.

44. An infusion pump as defined in claim 40 wherein said means for prompting a user of the infusion pump to input a plurality of infusion parameters comprises:

means for prompting the user for a first dose mode selected from the group of dose modes consisting of micrograms/kilogram/minute, milligrams/kilogram/hour, micrograms/kilogram/hour, and milligrams/kilogram/minute; and means for prompting the user for a second dose mode selected from the group of dose modes consisting of micrograms/minute, milligrams/minute, milligrams/hour, and units/hour.

* * * * *

UNITED STATES PATENT AND TRADEMARK OFFICE
CERTIFICATE OF CORRECTION

PATENT NO. : 5,609,575

DATED : MARCH 11, 1997

INVENTOR(S) : STELLA D. LARSON, ANNE F. MICKELSON, PETER M. EISENBERG

It is certified that error appears in the above-indentified patent and that said Letters Patent is hereby corrected as shown below:

Col. 4, line 15, delete "frown", insert --from--

Col. 5, line 25, delete "meg", insert --mcg--

Col. 6, line 21, delete "traits", insert --units--

Col. 9, line 24, delete "frown", insert --from--

Col. 11, line 26, delete "frown", insert --from--

Signed and Sealed this

Ninth Day of September, 1997

Attest:

BRUCE LEHMAN

Attesting Officer

Commissioner of Patents and Trademarks